(12) United States Patent
Chan (10) Patent No.: US 8,597,317 B2
(45) Date of Patent: Dec. 3, 2013

(54) METHOD FOR REPAIR OF ARTICULAR CARTILAGE DEFECT AND A DEVICE USED THEREIN

(75) Inventor: Wing-Pong Chan Chan, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 13/482,623

(22) Filed: May 29, 2012

(65) Prior Publication Data
US 2013/0011442 A1    Jan. 10, 2013

Related U.S. Application Data

(63) Continuation-in-part of application No. 12/825,287, filed on Jun. 28, 2010, now abandoned.

(30) Foreign Application Priority Data

Dec. 11, 2009 (TW) .............................. 98142566 A (51) Int. Cl.
A61B 17/32   (2006.01)
A61B 17/56   (2006.01)
A61B 17/00   (2006.01)

(52) U.S. Cl.
USPC .............................. 606/167; 606/53; 606/79

(58) Field of Classification Search
USPC .............................................. 606/167, 53, 79
See application file for complete search history.

(56) References Cited

U.S. PATENT DOCUMENTS

| | | | |
|---|---|---|---|
| 2004/0175820 A1* | 9/2004 | Shigematsu et al. | 435/287.1 |
| 2005/0125077 A1 | 6/2005 | Harmon et al. | |
| 2010/0076473 A1* | 3/2010 | Tawfik et al. | 606/167 |

* cited by examiner

Primary Examiner — Xiaozhen Xie
(74) Attorney, Agent, or Firm — WPAT, P.C.; Anthony King (57) ABSTRACT

The invention provides a single surgical procedure by using autologous platelet-rich fibrin (PRF) and cartilage fragments to solve problems of contamination during incubation of chondrocytes and transplant rejection in vivo, which has the benefit of a more efficient and shorter recovery time. The invention also provides a device for easily and rapidly cutting cartilage to cartilage fragments so as to reduce contamination of the implant and infection.

14 Claims, 4 Drawing Sheets

METHOD FOR REPAIR OF ARTICULAR CARTILAGE DEFECT AND A DEVICE USED THEREIN

CROSS-REFERENCE TO RELATED APPLICATIONS

This continuation-in-part application claims priority to U.S. Non-Provisional patent application Ser. No. 12/825,287, filed Jun. 28, 2010, now abandoned, which claims priority to Taiwan Patent Application No. 098142566, filed Dec. 11, 2009. All of which are hereby incorporated by reference in their entirety.

FIELD OF THE INVENTION

The present invention relates to a method for the repair of articular cartilage defects. Particularly, the invention provides a single surgical procedure and a device used in the procedure.

BACKGROUND OF THE INVENTION

The healthy cartilage of joints (articular cartilage) in humans and other mammals is characterized by a columnar growth pattern of chondrocytes, which produce a hyaline cartilage predominantly containing proteoglycans, type II collagen, and water. Articular cartilage, which covers each end of the long bones in vivo, is a smooth white structure. The structure of the articular cartilage is significantly different from that of the cortical bone beneath it. Articular cartilage does not have any blood vessels or neurons, so its nutrients are absorbed from the surrounding joint fluids, and thus, nutrients are provided slowly, resulting in relatively slow metabolism. Bone tissues have abundant blood vessels and nerve networks, such that their metabolism is very fast. Also, because a nerve system exists in bones, any impact or rubbing of two bones can be serious and painful. Because the surfaces of articulating bones in mammalian joints are covered with articular cartilage, bones do not come in direct contact with each other, so a person will not suffer discomfort when walking or performing intense movement. Articular cartilage provides an effective weight-bearing cushion to prevent bone-to-bone contact of opposing bones in a joint and, thus, is critical to the normal function of the joint.

Articular cartilage defects may be caused by wear over time, mechanical injuries or diseases. Many arthritic diseases and different degrees of trauma can cause destruction or deterioration of this fragile layer, leading to pain, joint stiffness, and even crippling disability. For example, joints are worn down over time; mechanical injuries are caused by accidents, causing the cartilage to tear and break down; and cartilage is eroded because of diseases, such as gout, rheumatoid arthritis and osteoarthritis. It is generally believed that, because articular cartilage lacks a vasculature, damaged cartilage tissue does not receive sufficient or proper stimuli to elicit a repair response. Once the articular cartilage becomes damaged, it cannot repair itself and therefore is worn down gradually. In addition, if the bone underneath the articular cartilage becomes damaged, pain or swelling may occur, resulting in difficulty walking and affecting daily life.

Since joint cartilage in adults does not naturally regenerate once it is destroyed, damaged adult articular cartilage has historically been treated with a variety of surgical interventions including repair, replacement, or excision. Articular cartilage defects have traditionally been treated with chondroplasty, shaving, microfracture, abrasion arthroplasty and, most recently, autologous transplantation. Early on, the treatment of articular cartilage defects was principally concerned with preventing a progression of the defect. More recently, attention has been focused on developing ways to actually repair the defect and effect articular cartilage healing. U.S. 2005/0125077 provides biocompatible tissue implants for repairing tissue injury or defects, wherein the tissue implants form a biological tissue slice that serve as a source of viable cells capable of tissue regeneration and/or repair, and can be harvested from healthy tissue to have a geometry that is suitable for implantation at the site of the injury or defect. However, this prior art reference did not teach nor suggest the optimal method for repair of articular cartilage defects. Moreover, the xenograft and xenogenous biomaterials may cause immunological problems, and the aforementioned is not the method most suitable for solving problems with the repair and treatment of articular cartilage defects.

Treatment of articular cartilage defects may be either surgical or non-surgical. Several operative procedures are currently used to repair or remove damaged cartilage in order to prevent further destruction of the joint, decrease pain, and restore function. These include arthroscopic debridement and lavage, subchondral bone stimulating procedures, transplantation of chondrocytes or cartilage autografts and allografts, and total knee arthroplasty. The traditional surgical process for treating articular cartilage defects or degeneration involves two procedures. In the first surgical procedure, a small biopsy of articular cartilage is performed, which is then transported to a laboratory specializing in cell culture for amplification. The tissue biopsy is treated with enzymes that release the chondrocyte cells from the matrix, and the isolated cells will be grown for a period of 3 to 4 weeks using standard tissue culture techniques. Once the cell population has reached a target number, the cells are sent back to the surgeon for implantation during a second surgical procedure. This manual labor-intense process is extremely costly and time consuming. Although clinical data suggests long term benefits for the patient, the prohibitive cost of the procedure combined with the traumatic impact of two surgical procedures to the knee have hampered adoption of this technique. Because the patient will have to endure the trauma of two surgical operations, the cartilage defects typically take a long time to repair. Furthermore, cell culture in vitro has many disadvantages, such as contamination.

Therefore, there remains a need for an effective method of repairing articular cartilage defects and injuries, one which can provide a time-saving surgical procedure, a faster recovery process, and beneficial reparative effects.

SUMMARY OF THE INVENTION

The invention provides a surgical method for repair and/or treatment of articular cartilage defect in a subject, comprising the steps of:
  (a) obtaining an autologous cartilage in the subject and mincing the autologous cartilage to plural cartilage fragments, wherein each of the minced cartilage fragments has a height, a width, and a depth, and said each of said height, width, and depth ranges in size from about 0.5 mm to 1.6 mm; and
  (b) implanting a mixture comprising the minced cartilage fragments and autologous platelet-rich fibrin (PRF) to the articular cartilage defect site, wherein the mixture does not contain any one member from the group consisting of a scaffold and a non-autologous implant.

The invention also provides a device for cutting cartilage, comprising:

a base having a cartilage holder assembled with the base for fixing the cartilage thereon, at least one compartment for collecting cartilage fragments, a pair of slide rails each respectively located at each of two parallel longitudinal sides of the base; and a blade holder slidably coupled to the base, and blade holder having a plurality of blades mounted at an underside of the blade holder;

the blade holder having two parallel longitudinal sides, and an inwardly extending lower flange and an upper flange at each of the two parallel longitudinal sides of the blade holder; the lower flange and upper flange define a space to receive the slide rail, wherein said pair of slide rails slidably engages with said blade holder, allowing said blade holder to move in a longitudinal direction relative to said base, thereby permitting said plurality of blades to slice into the cartilage.

DETAILED DESCRIPTION OF THE INVENTION

The invention provides a single surgical procedure by using autologous platelet-rich fibrin (PRF) and cartilage fragments to solve problems of contamination during incubation of chondrocytes and transplant rejection in vivo, which has the benefit of a more efficient and shorter recovery time. The invention also provides a device for easily and rapidly cutting cartilage into cartilage fragments so as to reduce contamination of the implant and infection.

Before any embodiments of the invention are explained in detail, it is to be understood that the invention is not limited in its application to the details of construction and the arrangement of components set forth in the following description and illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The invention provides a surgical method for repair and/or treatment of articular cartilage defect in a subject, comprising the steps of:

(a) obtaining an autologous cartilage in the subject and mincing the autologous cartilage to plural cartilage fragments, wherein each of the minced cartilage fragments has a height, a width, and a depth, and said each of said height, width, and depth ranges in size from about 0.5 mm to 1.6 mm; and (b) implanting a mixture comprising the minced cartilage fragments and autologous platelet-rich fibrin (PRF) to the articular cartilage defect site, wherein the mixture does not contain any one member from the group consisting of a scaffold and a non-autologous implant.

Preferably, the mixture further does not contain a cartilage slice and a cartilage strip.

According to the invention, a "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

According to the invention, the surgical method of the invention involves a single surgical procedure.

According to the invention, the damaged or destroyed articular cartilage is removed from the defective site before implantation.

According to the invention, the articular cartilage is autologous and not subjected to any physical, chemical and/or demineralization treatment. For example, the cartilage is not subjected to harsh chemical treatments, which can alter the inherent natural properties of material within the cartilage; the cartilage is preferably not subjected to demineralization treatments such as treatment with hydrochloric acid, ethylene diamine, and/or other demineralization agents; and the articular cartilage is preferably not subjected to elevated temperatures, e.g., temperatures greater than about 50° C. that may diminish the chondrogenic activity of the cartilage. However, the articular cartilage may be preserved, e.g., freeze-dried, frozen, and/or dried, after being removed from the joint.

According to the invention, the cartilage used in the method of the invention is minced to form cartilage fragments. The function of the minced cartilage fragments can be improved by reducing the size of the fragments. The smaller the fragment size, the better the function. Although according to previous research, stem cells may be the best cell source for cartilage tissue engineering, use of stem cells may need more than one operation for repair of articular cartilage defects. According to the invention, each of the minced cartilage fragments preferably has a height, a width and a depth and the each of the height, width and depth range in size from about 0.5 mm to about 1.6 mm. More preferably, the size ranges from about 0.5 mm to about 1.5 mm, about 0.5 mm to about 1.4 mm, about 0.5 mm to about 1.3 mm, about 0.6 mm to about 1.6 mm, about 0.6 mm to about 1.5 mm, about 0.6 mm to about 1.4 mm, about 0.6 mm to about 1.3 mm, about 0.6 mm to about 1.2 mm, about 0.6 mm to about 1.1 mm, about 0.6 mm to about 1.0 mm, about 0.6 mm to about 0.9 mm, about 0.6 mm to about 0.8 mm, about 0.6 mm to about 0.7 mm, about 0.9 mm to about 1.6 mm, about 0.9 mm to about 1.5 mm, about 0.9 mm to about 1.4 mm, about 1.0 mm to about 1.5 mm, about 1.0 mm to about 1.4 mm, about 1.0 mm to about 1.3 mm, about 1.1 mm to about 1.5 mm, about 1.1 mm to about 1.4 mm, about 1.1 mm to about 1.3 mm. Most preferably, the size is about 0.5 mm, about 0.6 mm, about 0.65 mm, about 0.7 mm, about 0.8 mm, about 0.9 mm, about 1.0 mm, about 1.1 mm, about 1.2 mm, about 1.3 mm, about 1.4 mm or about 1.5 mm. Preferably, the cartilage fragments are square. Cartilage fragments according to the present invention may be produced by grinding articular cartilage to produce fragments of the preferred sizes. The cartilage may be in the form of fresh cartilage, dry cartilage, freeze-dried cartilage, frozen cartilage, wet cartilage or mixtures thereof. Preferably, the cartilage is obtained from a part of the cartilage with no injuries in the mammal, for example, from normal cartilage adjacent to the injured cartilage. More preferably, the cartilage is obtained from femur cartilage in non-weight bearing site. According to the invention, at least a portion of femur cartilage is removed from the non-weight bearing site for surgical use. Preferably, the cartilage does not contain a cartilage slice or a cartilage strip.

The cartilage may be minced using any suitable grinding apparatus. For example, any grinding or cutting apparatus capable of grinding or cutting dry, hard, brittle material in seconds, such as turbo mills, disc mills, toothed disc mills, jet mills or other similar apparatuses are suitable. Preferably, grinding or cutting is performed under conditions that preclude raising the temperature of the articular cartilage to a level that may diminish the chondrogenic activity. For example, grinding or cutting is preferably performed without raising the temperature of the articular cartilage above about 50° C. In some embodiments, grinding or cutting is preferably performed without raising the temperature of the cartilage above 40° C. Continuous grinding in conventional grinding mills for 3-5 minutes can raise the temperature of the material to 70° C. or above. However, operating a grinding mill intermittently may preclude an undesirable rise in temperature.

In view of the facts that raising temperature would diminish the chondrogenic activity and result in a longer surgical time that would increase risks such as contamination of the implant and infection, the invention provides a device for cutting cartilage, comprising:

a base having a cartilage holder assembled with the base for fixing the cartilage thereon, at least one compartment for collecting cartilage fragments, a pair of slide rails each respectively located at each of two parallel longitudinal sides of the base;

a blade holder slidably coupled to the base, and blade holder having a plurality of blades mounted at an underside of the blade holder;

the blade holder having two parallel longitudinal sides, and an inwardly extending lower flange and an upper flange at each of the two parallel longitudinal sides of the blade holder; the lower flange and upper flange define a space to receive the slide rail, wherein said pair of slide rails slidably engages with said blade holder, allowing said blade holder to move in a longitudinal direction relative to said base, thereby permitting said plurality of blades to slice into the cartilage. Preferably, the plurality of blades are arranged in an array and an interval between each of the plurality of blades with an adjacent blade ranges from about 0.5 mm to about 1.6 mm.

According to the invention, the base of the device has a cartilage holder detachably assembled with the base for fixing the cartilage thereon and at least one compartment for collecting cartilage fragments. Preferably, there are two compartments in the base. In one embodiment, the base has a cartilage holder in the middle and two compartments at opposite sides of the holder. A pair of slide rails are each respectively located at each of two parallel longitudinal sides of the base so as to provide unrestricted sliding movement of the blade holder. In one embodiment, the cartilage holder has a circumferential wall having a plurality of slits wherein the width of each slit is larger than the thickness of each blade so that the blades can pass through the wall. In one embodiment, the cartilage holder has a pivoting member adapted for engagement with the base and to engage with the cartilage holder being joined for 360 degree rotation about a vertical axis therethrough. Preferably, rotation degree is 90°. As a result, the cartilage holder is rotable by 90°. In another embodiment, the base further comprises a lid fitted to and locked on said cartilage holder so as to fix the cartilage more securely, while having a plurality of slits wherein the width of each slit is larger than the thickness of each blade so that the blades can pass through the lid.

According to the invention, the blade holder is slidably coupled to the base and has a plurality of blades mounted at an underside of the blade holder wherein the plurality of blades are arranged in an array. Preferably, an interval between each of the plurality of blades with an adjacent blade ranges from about 0.5 mm to about 1.6 mm. Preferably, the interval ranges from about 0.5 mm to about 1.5 mm, about 0.5 mm to about 1.4 mm, about 0.5 mm to about 1.3 mm, about 0.6 mm to about 1.6 mm, about 0.6 mm to about 1.5 mm, about 0.6 mm to about 1.4 mm, about 0.6 mm to about 1.3 mm, about 0.6 mm to about 1.2 mm, about 0.6 mm to about 1.1 mm, about 0.6 mm to about 1.0 mm, about 0.6 mm to about 0.9 mm, about 0.6 mm to about 0.8 mm, about 0.6 mm to about 0.7 mm, about 0.9 mm to about 1.6 mm, about 0.9 mm to about 1.5 mm, about 0.9 mm to about 1.4 mm, about 1.0 mm to about 1.5 mm, about 1.0 mm to about 1.4 mm, about 1.0 mm to about 1.3 mm, about 1.1 mm to about 1.5 mm, about 1.1 mm to about 1.4 mm, about 1.1 mm to about 1.3 mm. Most preferably, the interval is about 0.5 mm. about 0.6 mm, about 0.65 mm, about 0.7 mm, about 0.8 mm, about 0.9 mm, about 1.0 mm, about 1.1 mm, about 1.2 mm, about 1.3 mm, about 1.4 mm or about 1.5 mm. The number of blades is designed depending on desired cartilage size. Preferably, the blade holder includes 8 to 20 blades; more preferably, 8 to 19, 8 to 18, 8 to 17, 8 to 16, 8 to 15, 8 to 14, 8 to 13, 8 to 13, 9 to 20, 9 to 19, 9 to 18, 9 to 17, 9 to 16, 9 to 15, 9 to 14, 9 to 13, 9 to 12, 10 to 15, 10 to 20, 10 to 19, 10 to 18, 10 to 17, 10 to 16, 10 to 15, 10 to 14, 10 to 13 or 10 to 12 blades; most preferably, 11 blades. Preferably, the blade is that of a scalpel.

The blade holder has two parallel longitudinal sides and an inwardly extending lower flange and an upper flange at each of the two parallel sides of the holder, and the lower flange and upper flange define a space receiving the slide rail of the base, so that said slide rails slidably engages with the space of the blade holder, allowing said blade holder to move in a longitudinal direction relative to said base thereby permitting said plurality of blades to slice into the cartilage and permitting said blade holder to be removed from or inserted into the base from the two sides of the base. According to the invention, the blade holder is removable from the base.

Figure 1A:
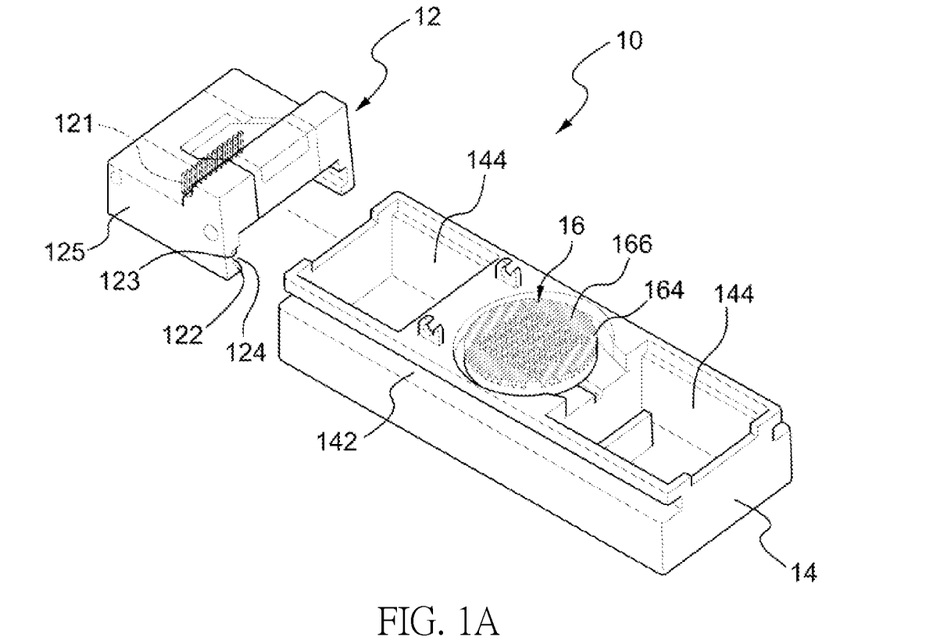
FIG. 1A shows a preferred embodiment of the device of the present invention.
Figure 1B:
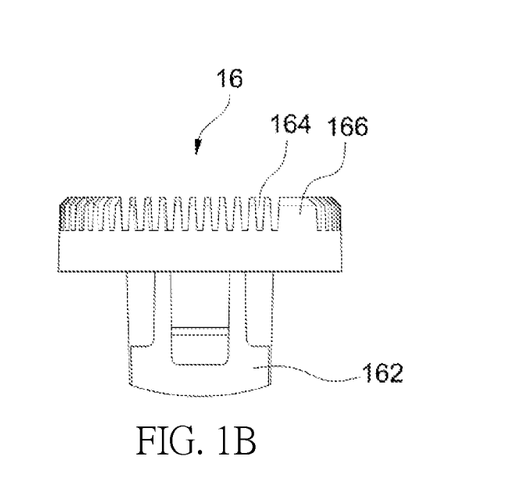
FIG. 1B shows an embodiment of the cartilage holder.
Figure 2:
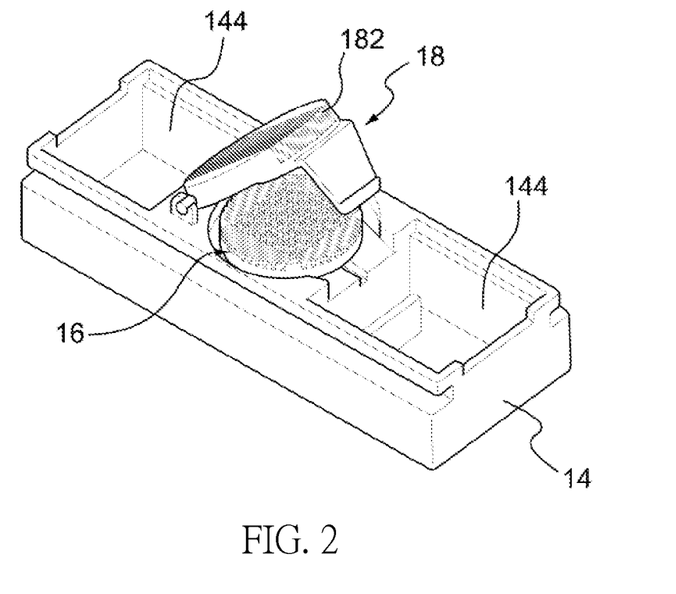
FIG. 2 shows an embodiment of the cartilage holder comprising a lid.

FIG. 1A is a preferred embodiment of the device of the present invention. The numeral 10 generally designates a device of the present invention. Device 10 includes a blade holder 12 and a base 14. The blade holder 12 includes a plurality of blades 121 (for example, eleven blades) mounted at an underside of the blade holder 12 and arranged in an array. The blade holder 12 has two parallel longitudinal sides 125. At each longitudinal side of the holder, there is an inwardly extending lower flange 122 and upper flange 123, and the lower flange and upper flange define a space 124 receiving the slide rail 142 of the base 14, so that said blade holder 12 may be moved in a longitudinal direction relative to said base 14, thereby permitting said plurality of blades 121 to slice into the cartilage, and permitting said blade holder 12 to be removed or inserted into the base 14 from the two sides of the base 14. The base 14 includes a cartilage holder 16 in the middle for fixing the cartilage thereon and two compartments 144 at opposite sides of the holder 16 for collecting cartilage fragments. FIG. 1B illustrates an embodiment of the cartilage holder 16. The cartilage holder 16 has a pivoting member 162 adapted for engagement with the base 14 being joined for 360 degree rotation about a vertical axis therethrough. In one embodiment, the cartilage holder 16 is rotatable by an angle; preferably, by 90°. The cartilage holder 16 has a circumferential wall 166 having a plurality of slits 164 wherein the width of each slit is larger than the thickness of each blade so that the blades 121 can pass through the wall 164. A pair of slide rails 142 is each respectively located at each of two parallel longitudinal sides of the base 14 so as to provide unrestricted sliding movement of the blade holder 12. Referring to FIG. 2, the base 14 further comprises a lid 18 fitted to and locked on said cartilage holder 16 so as to fix the cartilage more securely. The lid 18 has a plurality of slits 182 wherein the width of each slit is larger than the thickness of each blade so that the blades can pass through the lid.

The "platelet-rich fibrin" (PRF) used herein is an autologous platelet concentrate that is used to accelerate soft-tissue and hard-tissue healing. According to the invention, PRF refers to a second-generation platelet concentrate. David M. Dohan et al describe the preparation of a platelet rich solid fibrin network from whole blood without adding any additives or reagents (Part I: Technological concepts and evolution, Oral Surg Oral Med Oral Pathol Oral Radiol Ended 2006; 101:E37-44). The PRF protocol involves placing a blood sample without anticoagulant in 10-mL glass or glass coated plastic tubes, which are immediately centrifuged at approximately 400 g for 10 minutes. The absence of anticoagulant implies the activation, within a few minutes, of most of the platelets in contact with the glass tube walls and the release of the coagulation cascades. Fibrinogen is initially concentrated in the top part of the tube, before the circulating thrombin transforms it into fibrin. A fibrin clot is then obtained in the middle of the tube, extending from the upper part of the red corpuscles at the bottom of the tube to the cellular plasma at the top. Platelets are trapped massively in the fibrin meshes. The success of this technique entirely depends on the speed of blood collection and transfer to the centrifuge. Indeed, without anticoagulant, the blood samples start to coagulate almost immediately upon contact with the tube glass, and it takes a minimum of a few minutes of centrifugation to concentrate fibrinogen in the middle and upper part of the tube. Quick handling is the only way to obtain a clinically usable PRF clot. If the duration required to collect blood and launch centrifugation is overly long, failure will occur: The fibrin will polymerize in a diffuse way in the tube and only a small blood clot lacking consistency will be obtained. In conclusion, the PRF protocol makes it possible to collect a fibrin clot charged with serum and platelets. By removing the clot from the tube, manually cutting the red cells apart, and manually driving out the fluids trapped in the fibrin matrix (serum), practitioners will obtain autologous fibrin membranes. Alternatively, PRF obtained from blood in the mammal is collected in a container which holds a separator polyester gel, and then centrifuged at a speed in the range of 1000 to 5000 rpm for 1 to 20 minutes. The centrifuge time is adjusted according to the centrifuge speed. Additionally, the blood may be centrifuged twice so as to obtain different concentrations of PRF.

PRF is a fibrin glue that acts as a plug that traps most light blood components, such as platelets and leucocytes, as well as circulating molecules, such as growth factors and fibronectin (Dohan, D M et al. (2006) *Platelet-rich fibrin (PRF): a secondgeneration platelet concentrate. Part I: technological concepts and evolution. Oral Surg. Oral Med. Oral Pathol. Oral Radiol. Endod.* 101, e37-e44; Dohan, D. M. et al. (2006) *Platelet-rich fibrin (PRF): a second generation platelet concentrate. Part II: platelet-related biologic features. Oral Surg. Oral Med. Oral Pathol. Oral Radiol. Endod.* 101, e45-e50; Dohan D M, Rasmusson L, Albrektsson T. (2009), *Classification of platelet concentrates: from pure platelet-rich plasma (P-PRP) to leucocyte- and platelet-rich fibrin (L-PRF). Trends Biotechnol.* 27(3):158-67). Fibrin is the activated form of a plasmatic molecule called fibrinogen (Dohan, D. M. et al. (2006) *Platelet-rich fibrin (PRF): a second generation platelet concentrate. Part II: platelet-related biologic features. Oral Surg. Oral Med. Oral Pathol. Oral Radiol. Endod.* 101, e45-e50). It is formed from fibrinogen by the protease thrombin, and is then polymerised to form a "mesh" that forms a hemostatic plug or clot (in conjunction with platelets) over a wound site (Dohan, D M et al. (2006) *Platelet-rich fibrin (PRF): a second generation platelet concentrate. Part I: technological concepts and evolution. Oral Surg. Oral Med. Oral Pathol. Oral Radiol. Endod.* 101, e37-e44). Fibronectin is a high-molecular weight (~440 kDa) glycoprotein of the extracellular matrix that binds to membrane-spanning receptor proteins called integrins. Since fibrinogen and fibronectin do not have a polymerized structure similar to PRF, they cannot act as a plug that traps most light blood components and achieve the function of PRF.

During the process of PRF formation, blood is collected without any anticoagulant and immediately centrifuged. A natural coagulation process then occurs and allows for the easy collection of a leucocyte- and platelet-rich fibrin (L-PRF) clot, without the need for any biochemical modification of the blood, that is, no anticoagulants, thrombin or calcium chloride are required. The fibrin network and content of PRF are significantly different from those of PRP mentioned in U.S.2005/0125077. The fibrin network of PRP is bilateral junction, whereas PRF is equilateral junction. Moreover, the platelet-related biologic features of PRP and PRF are also significantly different. The formation of PRP requires addition of bovine thrombin, which imposes a potential risk caused of viral infection and rejection. In addition, thrombin concentration affects fibrin polymerization of PRP. Variation of thrombin concentration may cause inconsistent polymerization. In contrast, the formation of PRF does not require addition of anticoagulants, thrombin or calcium chloride, so the fibrin network of PRP formed by natural polymerization is most suitable for seeding cells and growth factors. PRF comprises many kinds of growth factors and cytokines. The growth factors may comprise a transforming growth factor, a platelet-derived growth factor, an epidermal growth factor, a vascular endothelial growth factor, an insulin-like growth factor, or a combination thereof. The transformative growth factor, such as TGFβ-1, can promote cell growth and differentiation, and regulate immune functions. In addition, the cytokines may comprise interleukins, such as IL-6, IL-1β or IL-4, or tumor necrosis factors, such as TNF-α. Therefore, the composition according to the present invention has the cytokines needed for inflammatory responses and repair responses to promote normal immune responses in mammals. PRF can be used in conjunction with bone grafts; such a combination offers several advantages, such as promoting wound healing, bone growth and maturation, graft stabilization, wound sealing and hemostasis, and improving the handling properties of graft materials.

The invention also provides a system for repair and/or treatment of articular cartilage defect, comprising a centrifuge machine, a cutting device and a stirring device. The size of the supporting tool is convenient for placing in an operation room. The centrifuge machine is arranged for centrifuging blood to obtain platelet-rich fibrin (PRF), with the centrifugation speed thereof at least 1000 to 5000 rpm. The cutting device is arranged for cutting cartilage under sterilized conditions. The stifling device is for mixing the PRF and the cartilage.

The method and device of the invention provide one or more of the following advantages:

(1) When defective cartilage is removed from a mammal during the first surgical operation, the PRF and cartilage fragments are implanted into the injury site. Therefore, the articular cartilage defect is repaired by a single surgical procedure, and there is no need to perform a second surgical operation on the mammal. In view of the single surgical procedure, the time needed for the operation and the surgical risk and suffering of patient can be greatly reduced.
(2) Because the PRF and cartilage fragments according to the present invention are obtained autologously, transplant rejections are avoided.
(3) The PRF used in the present invention can induce growth factors to activate normal immune responses, accelerate blood vessel regeneration, and at the same time induce aggregation and differentiation of cyclic adult stem cells and mesenchymal stem cells (MSCs) in vivo to speed up tissue regeneration.

EXAMPLE

Example 1

Use of Cartilage Fragments in Combination with PRF in the Single Surgical Procedure Preparation of PRF Pigs are selected for use as laboratory animals in the present embodiment. Six ml blood is drawn from the pigs. The blood is collected in a container, such as a centrifuge tube, holding a separator polyester gel, and in the present embodiment, the centrifuge tube is used to contain the blood. The centrifuge tube containing the blood is centrifuged at a speed in the range of 1000 to 5000 rpm for 1 to 20 minutes, and preferably, also at 2500 to 3500 rpm for 8 to 12 minutes. The centrifuge time may be adjusted according to the centrifuge speed. After centrifugation, jelly-like PRF is obtained in the middle part of the centrifuge tube, and then sterile forceps are used to clip the jelly-like PRF out. All steps in the preparation of the PRF are performed under standard disinfection procedures. The 6 ml whole blood may yield 1-1.5 ml of PRF. The size of the autologous PRF is about 0.75 cm$^3$.

Surgical Procedure

Each pig is subjected to operations on the medial condylar surfaces of the distal femurs of both legs, such that each pig has two injuries, one in each leg, with diameters of 8 mm and depths of 5 mm, which imitate cartilage defects. The 16 pigs are divided into 4 groups: the PRF group, the P/C group, the CAR group, and the control group, according to the implantation substance, and thus, each group has 8 cartilage defects. Table 1 shows details of the implanted substances in each group.

TABLE 1

Each group and implantation substances thereof in the present embodiment

| Group | Implantation substances |
|---|---|
| PRF group | Autologous PRF only |
| P/C group | Autologous PRF and autologous cartilage fragments |
| CAR group | Autologous cartilage fragments only |
| Control group | No implanting of any substances; imitation of cartilage defects only |

Six months after transplantation, the pigs in each group are sacrificed to analyze the degree of regeneration of the cartilage defect by means of a gross grading scale. The items in the gross grading scale include coverage, neo-cartilage color, defects in margins, and surface smoothness. Under the parameters of coverage, coverage of the regenerated cartilage over 75% on the medial condyle is defined as 4, and coverage ranges of 50-75%, 25-50%, less than 25% and without regenerated cartilages are defined as grades 3, 2, 1 and 0, respectively. The five degrees of neo-cartilage color are as follows: normal (white), 25% yellowish-brown, 50% yellowish-brown, 75% yellowish-brown and 100% yellowish-brown, defined as 4, 3, 2, 1 and 0, respectively. The margin defects are categorized as follows: no visible margin defect, 25% margin visibly defective, 50% margin visibly defective, 75% margin visibly defective and entire margin visibly defective are defined as 4, 3, 2, 1 and 0, respectively. Finally, the five degrees of surface smoothness are: smooth/level with normal surfaces, smooth but raised, 20-50% irregular, 50-75% irregular, and more than 75% irregular, defined as 4, 3, 2, 1, and 0, respectively. Therefore, the higher the score on the gross grading scale, the better the regeneration and recovery.

For the coverage of regenerated cartilage, the results indicate that the amount of regenerated cartilage in the control group is obviously inadequate. For example, the coverage of the regenerated cartilage in five cartilage defects is less than 50%, and one cartilage defect is still hollow without regenerated cartilage. Compared with the control group, the coverage of regenerated cartilage in the PRF group in the six cartilage defects reaches more than 75%. In the CAR group, the coverage in four cartilage defects reaches 50%, and the coverage in two cartilage defects reaches only 25%. In the P/C group, the coverage of regenerated cartilage in all cartilage defects reaches more than 75%. In the neo-cartilage color analysis, the color of the regenerated cartilage in the PRF group and the CAR group range between white and red. But the color of the regenerated cartilage in the P/C group is white, and the surface of the regenerated cartilage is smooth, without damage in the margins. Table 2 shows the results from the gross grading scale.

TABLE 2

The results of the gross grading scale in each group in the example.

Values are mean ± standard deviation.

| Group | Coverage | Neo-cartilage color | Defective margins | Surface smoothness |
|---|---|---|---|---|
| PRF group | 2.75 ± 0.31 | 1.97 ± 0.35 | 1.90 ± 0.24 | 1.53 ± 0.33 |
| P/C group | 3.56 ± 0.28 | 2.88 ± 0.31 | 2.88 ± 0.27 | 2.90 ± 0.24 |
| CAR group | 2.93 ± 0.28 | 2.34 ± 0.33 | 2.31 ± 0.33 | 2.50 ± 0.31 |
| Control group | 1.59 ± 0.27 | 1.78 ± 0.22 | 1.13 ± 0.26 | 0.78 ± 0.27 |

The microstructure of the regenerated cartilage is analyzed by a histological scaling assessment. The histological scaling assessment of regenerated cartilage has six parameters: surface, matrix, cell distribution, cell population, subchondral bone and cartilage mineralization. The surface of regenerated cartilage being continuous and smooth is defined as 3, and the surface of regenerated cartilages being crude is defined as 0. For the matrix of regenerated cartilage, hyaline, hyaline/fibrocartilage, fibrocartilage and fibrous tissue are defined as 3, 2, 1 and 0, respectively. For the cell distribution of regenerated cartilage, columnar, columnar-cluster, cluster and individual cells/disorganized are defined as 3, 2, 1 and 0, respectively. For the cell population of regenerated cartilage, predominantly viable, partially viable and less than 10% viable are defined as 3, 1 and 0, respectively. For subchondral bone, normal, increased remodeling, bone necrosis/granulation tissue, detached/fracture/callus at base are defined as 3, 2, 1 and 0, respectively. Finally, for mineralization of the regenerated cartilage, normal and abnormal/inappropriate are defined as 3 and 0, respectively. Higher score indicates that the microstructure of the regenerated cartilage is more complete. Table 3 shows the results of the histological scaling assessment.

TABLE 3

The results of the histological scaling assessment in each group in the example.

| Group | Values are mean ± standard deviation. | | |
|---|---|---|---|
| | Surface | Matrix | Cell distribution |
| PRF group | 2.79 ± 0.27 | 1.14 ± 0.28 | 1.14 ± 0.28 |
| P/C group | 2.86 ± 0.29 | 2.18 ± 0.24 | 2.36 ± 0.32 |
| CAR group | 2.79 ± 0.30 | 1.79 ± 0.27 | 1.82 ± 0.19 |
| Control group | 1.00 ± 0.29 | 0.96 ± 0.22 | 0.64 ± 0.20 |

| Group | Values are mean ± standard deviation. | | |
|---|---|---|---|
| | Cell population | Subchondral bone | Cartilage mineralization |
| PRF group | 2.25 ± 0.29 | 2.00 ± 0.20 | 1.50 ± 0.20 |
| P/C group | 2.68 ± 0.35 | 2.43 ± 0.28 | 2.14 ± 0.31 |
| CAR group | 2.32 ± 0.35 | 2.14 ± 0.24 | 1.68 ± 0.35 |
| Control group | 2.21 ± 0.27 | 1.64 ± 0.20 | 0.68 ± 0.19 |

To sum up the results, the scores for the matrix, the cell distribution and cartilage mineralization of the regenerated cartilages in the P/C group are significantly higher than those in the other three groups. Therefore, the microstructure of the regenerated cartilage in the P/C group is more complete than that in the other three groups.

Figure 3:
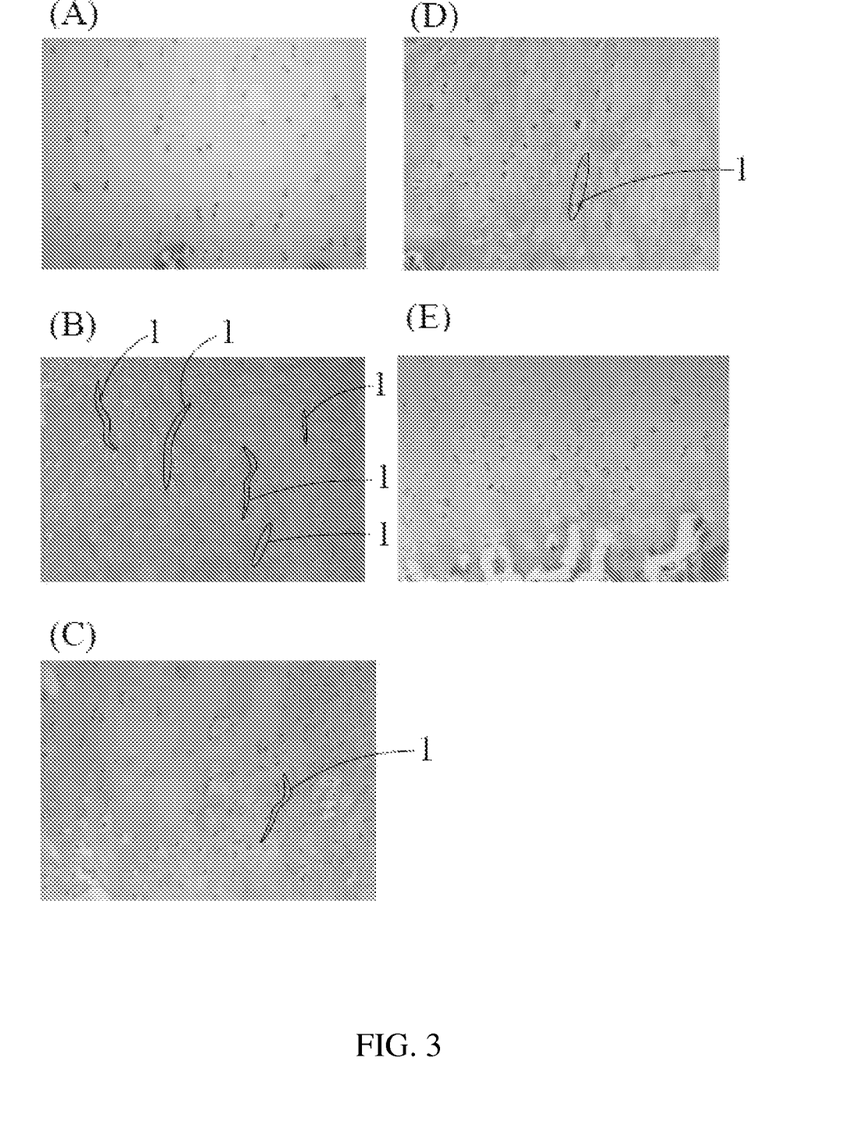
FIG. 3 shows H&E staining of the regenerated cartilage matrix with the composition disclosed by the present invention.

FIG. 3 shows H&E staining pictures of the regenerated cartilage matrix with the composition according to the present invention. As shown, sections (A), (B), (C), (D) and (E) in FIG. 3, represent non-damaged cartilage, the control group, the PRF group, the CAR group and the P/C group, respectively. Most of the matrixes of the regenerated cartilage in the PRF group and the CAR group are integrated with hyaline cartilage and fibrous cartilage. The fibrous cartilage is usually converted to hard bone by ossification. The amount of fibrous cartilage in the P/C group is lower, and the section of the P/C group is similar to the section of the non-damaged cartilage.

Figure 4:
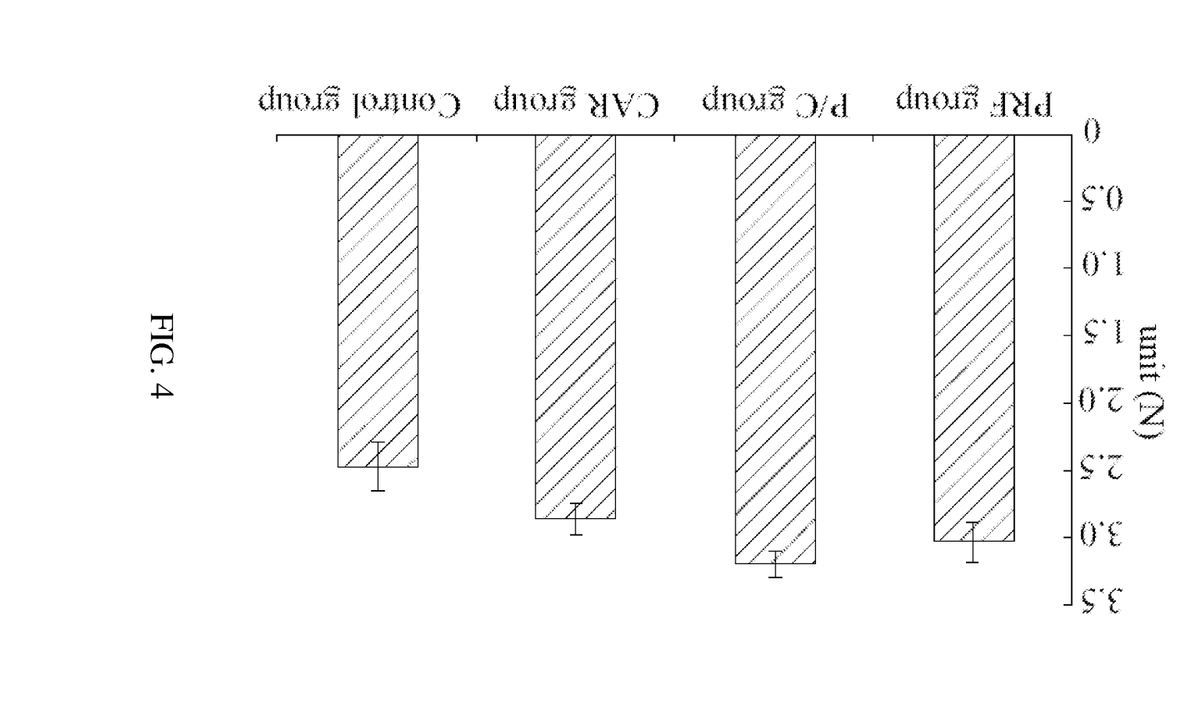
FIG. 4 shows a bar chart which indicates the results of a compressive stiffness test in regenerated cartilage.

FIG. 4 shows a bar chart illustrating the results of a compressive stiffness test on regenerated cartilage. As shown, the Newton (N) value in the P/C group is higher than in the other three groups. The major function of cartilage is to prevent contact of two hard bones. Therefore, the higher the Newton value in the compressive stiffness test, the better the neo-cartilage function.

Accumulations of sulphate-glycosaminoglycans (s-GSGs) are revealed and analyzed by Alcian blue staining. In normal cartilage, s-GSGs accumulate in the extra-chondrocyte matrix, so that it is presented as a uniform blue color. In the PRF group and the CAR group, the staining results range between those of the repaired cartilage and the non-damaged cartilage. However, the staining results in the P/C group and normal cartilage are similar, indicating that the repair efficacy in the P/C group is better. Furthermore, accumulation of proteoglycans in extra-chondrocytes are revealed and analyzed by safranin O. The results show the color of the regenerated cartilage in the P/C group is stronger than that in the PRF group and the CAR group, and is similar to that of the normal cartilage.

In summary, when the composition according to the present invention is used to treat an articular cartilage defect in a mammal (in the P/C group), the repair efficiency is higher than that of the other groups. When defective cartilage is removed by a surgical operation, the composition is implanted into the injury site at the same time, thereby repairing the cartilage defect. Thus, there is no need to perform a second surgical operation. The materials used in the surgery are obtained autologously from a mammal, thereby obviating transplant rejection. The composition comprises PRF, and PRF comprises growth factors to activate normal immune responses. The growth factors can accelerate blood vessel regeneration, and at the same time induce aggregation and differentiation of cyclic adult stem cells and mesenchymal stem cells (MSCs) in vivo. In addition, because the composition comprises an autologous cartilage fragment and the autologous cartilage fragment can act as a scaffold to speed up tissue regeneration.

The present invention has been described with some preferred embodiments thereof, and it is understood that many changes and modifications in the described embodiments can be carried out without departing from the scope and the spirit of the invention, which is intended to be limited only by the appended claims.

Comparative Example

Use of Device of the Invention to Obtain Cartilage Fragments

Cartilage having diameter of around 1 cm was cut from autologous femur cartilage, and the resulting cartilage was subjected to the cutting device illustrated in the invention to obtain cartilage fragments. The cartilage holder of the device was then rotated an angle of 90° and the resulting fragments were then minced with the cutting device again to obtain square fragments with a size of around $4.096(1.6^3)$-$0.125(0.5^3)$ mm$^3$. For example, by using a cutting device wherein the blade holder has 11 blades and an interval between each of the blades with an adjacent blade is around 1.3 mm, more than 60 cartilage fragments with 1.3 mm×1.3 mm×1.3 mm ($1.3^3$ mm$^3$) can be obtained after cutting twice wherein the second time was performed by rotating the cartilage holder by 90°. These fragments were used in surgery and can be expected to obtain advantageous effects in implantation because smaller cartilage fragments can be obtain and used in implantation by using the cutting device of the invention.

What is claimed is:

1. A device for cutting cartilage, comprising:
   a base having a cartilage holder assembled with the base for fixing the cartilage thereon, at least one compartment for collecting cartilage fragments, a pair of slide rails each respectively located at each of two parallel longitudinal sides of the base; and
   a blade holder slidably coupled to the base, and blade holder having a plurality of blades mounted at an underside of the blade holder;
   the blade holder having two parallel longitudinal sides, and an inwardly extending lower flange and an upper flange at each of the two parallel longitudinal sides of the blade holder; the lower flange and upper flange define a space to receive the slide rail, wherein said pair of slide rails slidably engages with said blade holder, allowing said blade holder to move in a longitudinal direction relative to said base, thereby permitting said plurality of blades to slice into the cartilage.

2. The device of claim 1, wherein the cartilage holder is detachably assembled with the base.

3. The device of claim 1, wherein the base contains two compartments.

4. The device of claim 1, wherein the base has a cartilage holder in the middle and two compartments at opposite sides of the holder.

5. The device of claim 1, wherein the cartilage holder has a circumferential wall having a plurality of slits wherein the width of each slit is larger than the thickness of each blade so that the blades can pass through the wall.

6. The device of claim 1, wherein the cartilage holder has a pivoting member adapted for engagement with the base, being joined for 360 degree rotation about a vertical axis therethrough.

7. The device of claim 6, wherein the rotation degree is 90°.

8. The device of claim 1, wherein the base further comprises a lid fitted to and locked on said cartilage holder and the lid has a plurality of slits wherein the width of each slit is larger than the thickness of each blade so that the blades can pass through the lid.

9. The device of claim 1, wherein the plurality of blades are arranged in an array and an interval between each of the plurality of blades with an adjacent blade ranges from about 0.5 mm to about 1.6 mm.

10. The device of claim 9, wherein the interval between each blade ranges from about 0.5 mm to about 1.4 mm.

11. The device of claim 9, wherein the interval between each blade is about 1.0 mm to about 1.3 mm.

12. The device of claim 1, wherein the blade holder is removable from the base.

13. The device of claim 1, wherein the blade holder includes 8 to 15 blades.

14. The device of claim 1, wherein the blade holder includes 11 blades.

* * * * *

UNITED STATES PATENT AND TRADEMARK OFFICE
CERTIFICATE OF CORRECTION

PATENT NO. : 8,597,317 B2  Page 1 of 1
APPLICATION NO. : 13/482623
DATED : December 3, 2013
INVENTOR(S) : Wing-Pong Chan It is certified that error appears in the above-identified patent and that said Letters Patent is hereby corrected as shown below:

On the title page item (75) "Wing-Pong Chan Chan" should read --Wing-Pong Chan--

Signed and Sealed this
Twentieth Day of May, 2014

Michelle K. Lee
*Deputy Director of the United States Patent and Trademark Office*